(12) United States Patent  
Salik (10) Patent No.: US 8,784,445 B2  
(45) Date of Patent: Jul. 22, 2014

(54) ENDOVASCULAR FILTER AND RETRIEVAL APPARATUS

(76) Inventor: Erez Salik, Westport, CT (US)

(*) Notice: Subject to any disclaimer, the term of this patent is extended or adjusted under 35 U.S.C. 154(b) by 163 days.

(21) Appl. No.: 13/193,482

(22) Filed: Jul. 28, 2011

(65) Prior Publication Data

US 2012/0078286 A1 Mar. 29, 2012

Related U.S. Application Data

(60) Provisional application No. 61/369,115, filed on Jul. 30, 2010.

(51) Int. Cl.
*A61M 29/00* (2006.01)

(52) U.S. Cl.
USPC .......................................................... 606/200

(58) Field of Classification Search
USPC ........... 606/159, 200; 604/104–107; 623/1.36
See application file for complete search history.

(56) References Cited

U.S. PATENT DOCUMENTS

| 8,029,529 | B1* | 10/2011 | Chanduszko | 606/200 |
| 2003/0130680 | A1* | 7/2003 | Russell | 606/200 |
| 2004/0158273 | A1* | 8/2004 | Weaver et al. | 606/200 |
| 2005/0277977 | A1* | 12/2005 | Thornton | 606/200 |
| 2007/0191880 | A1* | 8/2007 | Cartier et al. | 606/200 |
| 2008/0039891 | A1* | 2/2008 | McGuckin et al. | 606/200 |

FOREIGN PATENT DOCUMENTS

WO  WO 2007/079413  *  7/2007  ............ A61M 29/00

* cited by examiner

*Primary Examiner* — Thomas McEvoy

(57) ABSTRACT

An intravascular filter comprising a plurality of struts extending from a central hub. The distal ends of the struts are curved to form an anchor in the vessel wall. The hub has a hook for retrieving the filter. The filter may be removed by employing a torque force to the hook, so as to disengage the strut ends from the vessel wall.

16 Claims, 8 Drawing Sheets

FIG. 20A  FIG. 20B

ENDOVASCULAR FILTER AND RETRIEVAL APPARATUS

CROSS-REFERENCE TO RELATED APPLICATIONS

This application claims priority to provisional application No. 61/369,115 filed Jul. 30, 2010.

FIELD OF THE INVENTION

The present invention is in the field of medical devices. More particularly, the present invention is in the field of endovascular filters that can be placed permanently or temporarily inside a human blood vessel for the purpose of trapping blood clots or debris and intercepting emboli.

BACKGROUND OF THE INVENTION

Pulmonary embolism (PE) is a blockage of the main artery of the lung or one of its branches by displaced clot or debris that has traveled from elsewhere in the body through the bloodstream. PE is a potentially life threatening condition with an annual incidence of approximately 600,000 cases. Prompt diagnosis and treatment of PE can dramatically reduce the morbidity and mortality associated with the condition. First-line therapy for PE is anticoagulation. For those patients in who anticoagulation is ineffective or inappropriate, intravascular filters can be deployed. These filters are designed to capture potentially fatal clots or debris from traveling into the lungs, most commonly from pelvic or lower extremity veins, or less commonly from the upper extremity veins. As such, filters are placed most commonly in the inferior vena cava (IVC) or superior vena cava (SVC), respectively. In many instances, the filter is placed permanently in the body. However, in those clinical circumstances where the risk of thromboembolism is impermanent, the temporary placement and subsequent retrieval of the filter may be preferable.

Generally, the quality of a filter is measured by at least some of the following characteristics: effectiveness in capturing blood clots without disrupting the normal flow of blood within the vessel, reliability in being deployed at a predictable location within the desired vessel, ability to remain in the deployed location without migration, ability to deploy and retrieve with minimal trauma to the vessel, structural integrity to allow for permanent deployment when desired, and allowing for a small deployment and retrieval system. Although multiple filter designs have been proposed, the difficulty in achieving these potentially conflicting objectives allows for improvement to the current designs. In particular, the objectives of having the filter securely anchored to the wall while also being readily detachable at any time have been difficult to assimilate into an effective design. Many prior art retrievable filters require that the removal force be in a vector parallel to the longitudinal axis of the blood vessel. At the same time, the filter must resist displacement in this same direction, to prevent migration into less optimal locations, including the heart and lung. Some filters attempt to minimize engagement with the blood vessel in order to facilitate subsequent removal. But this requires compromise in other aspects of the ideal filter, for example resistance to migration. Other designs, conceding the difficulty in achieving these disparate goals, abandon the concept of a fully retrievable filter and rely on a permanently embedded portion to optimize anchoring and centering of the filter. U.S. Pat. No. 6,506,205 is an example of such a design.

The design of the present invention improves on shortcomings in the prior art filter devices by altering the force necessary for retrieval from a longitudinal force to a predominantly rotational force. The disparate objectives of resistance to migration in the longitudinal direction, and extraction by a longitudinal force, are therefore ameliorated. In addition, altering the force required for retrieval can allow for retrieval of the filter from an upstream (e.g. femoral vein) approach. The design allows for secure anchoring, a self-centering conical filter element, with minimal vessel trauma during deployment and extraction and structural integrity to allow for permanent implantation when desired.

SUMMARY OF THE INVENTION

The present invention describes an intravascular filter which may be securely anchored to the vessel wall for permanent placement, and can be extracted when so desired. A preferred embodiment of the filter comprises a plurality of struts that extend from an apical hub towards the surface of the vessel wall. In one embodiment, the struts may be of variable length, and the angle of a strut relative to the longitudinal axis of the vessel may be adapted to allow contact with the surface of the vessel wall. The struts may also pivot at the hub to adapt to allow contact with the surface of the vessel wall. All struts, both long and short, terminate in a footplate which lies along a short arc on the vessel wall, conforms to the curve of the vessel, and aids in both centering and anchoring the filter. The footplate is oriented at an angle relative to the long axis of the vessel, and relative to the strut, so as to facilitate extraction by a torque force to disengage the filter from the vessel. By increasing the points and/or planes of contact between the filter and the vessel wall along the longitudinal axis of the vessel, this array may improve the ability of the central hub to remain centered within the vessel. In one embodiment the filter legs extend from an apical hub, positioned at the proximal (downstream) end of the filter, with the legs extending outward towards the vessel wall in a straight radial direction relative to the central long axis of the vessel. Just prior to the point of contact with the vessel wall, the legs angle to form the anchoring footplate of the filter. In another embodiment, the filter legs are spirally arranged, also terminating in a more acutely angled footplate that provides the centering and anchoring properties of the filter. The struts of the filter can be adapted so that the torque imparted on the struts through the hub causes winding and therefore foreshortening of the struts. This could allow capture of the filter form the foot end or inversion of the filter, and thereby allow for retrieval from an upstream (e.g. femoral vein) approach.

DETAILED DESCRIPTION OF THE INVENTION

Figure 1:
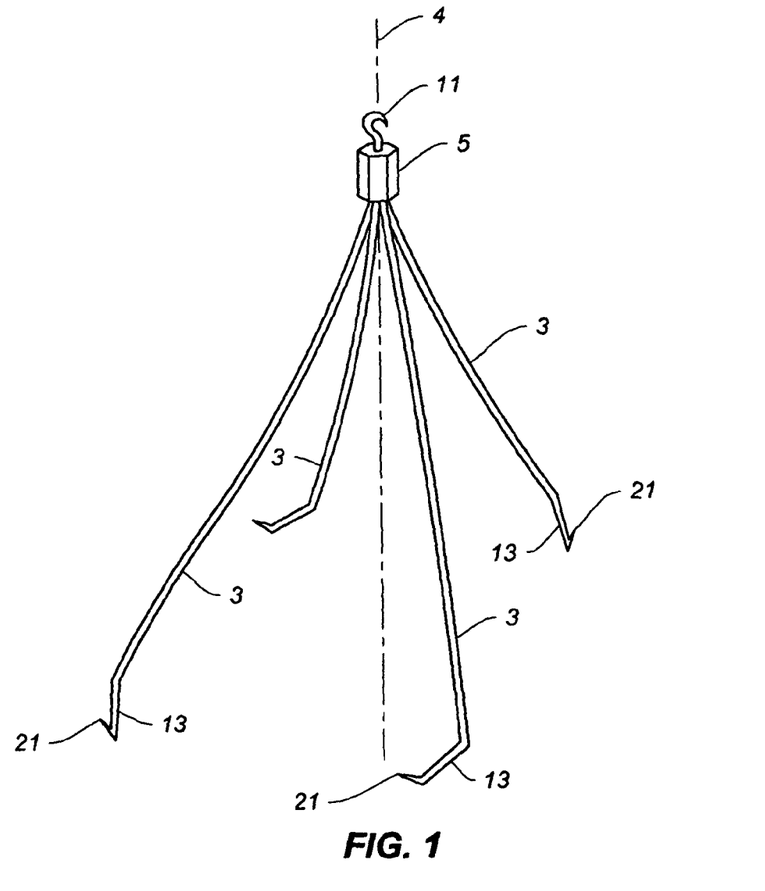
FIG. 1 is a side view of one embodiment of the vascular filter described herein. The figure depicts only four of six legs (the four in the foreground) of this embodiment.

An embodiment of the present invention will be discussed with reference to FIGS. 1-4 in which filter (1) is shown. FIG. 1 illustrates a filter (1). FIG. 1 illustrates only four struts (3), though the embodiment of FIG. 1 is contemplated to comprise six primary struts (3), each having first ends that emanate from a hub (5). Fewer or greater struts (3) may also be employed in other embodiments. The hub (5) draws together the primary struts (3) together to define a central or longitudinal axis of the filter (4), and confers a substantially conical shape to the filter (4). The hub (5) can be welded, press-fit or otherwise bonded to the struts (3) using techniques commonly known in prior art. As such, a force, such as a torque, that is imparted on the hub (5) would be transmitted to the struts (3). The proximal end of the hub (5) may have a retrieval section that terminates in a hook (11). In other embodiments, the proximal end of the hub (5) may have a retrieval section that terminates in other shapes, such as a loop or other shape or structure allowing for retrieval In addition to securing the struts, the hub may be configured to allow transmission of a torque force from the hub to the struts, for example to facilitate filter extraction. The struts can be formed from stainless steel wire, Nitinol, MP35N, or any suitable superelastic material that will result in a self-opening, self-expanding, and/or self remolding filter. In one embodiment, the hub (5) secures the first ends of individual struts (3) in a compact bundle.

Figure 2:
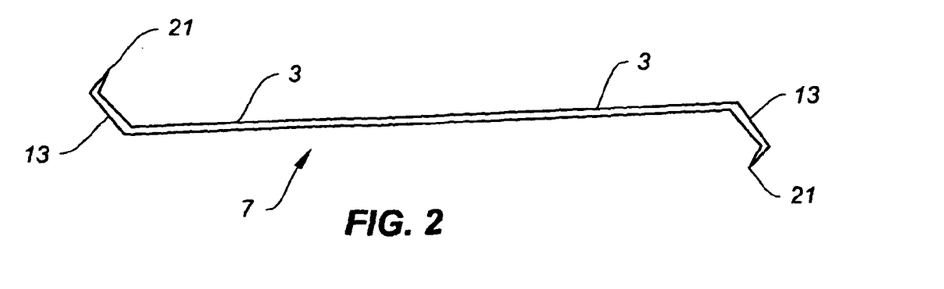
FIG. 2 is a side view of paired struts and anchoring footplates.
Figure 3:
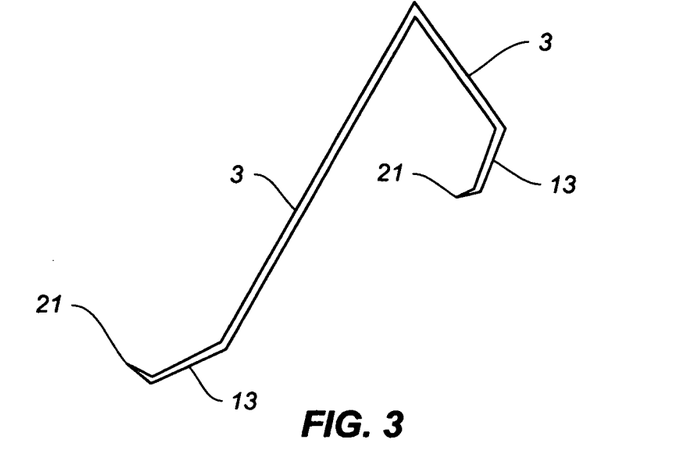
FIG. 3 depicts how paired struts can be formed from a single filament.

In another embodiment, as illustrated in FIG. 2 and FIG. 3, paired struts can be formed from a single filament (7) which is folded along the length of the filament to create paired struts of the desired length (3). The central hub can secure several of these folded filaments at the apex or a confluence of the various folding points.

Referring to FIGS. 1-3, the distal ends of the struts create footplates (13) which serve as the points and/or planes of contact between the filter and the vessel, and function to anchor, stabilize and center the filter within the vessel.

Figure 4:
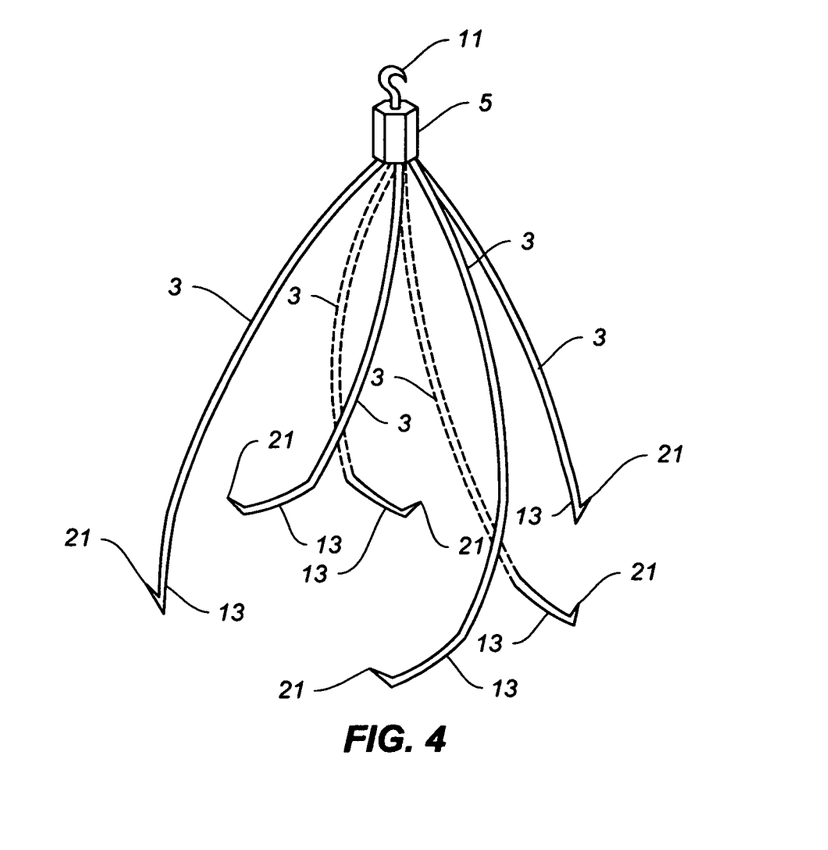
FIG. 4 is a side view of an alternative embodiment of the vascular filter, with struts emanating in an arc from the central hub.

FIG. 1 and FIG. 4 depict an embodiment for the present invention where struts (3) vary in length such that alternating legs are equal in length. Other embodiments consistent with the present invention may include different lengths of struts (3) and/or a different sequence of strut lengths. In the embodiment depicted in FIGS. 1 and 4, the struts (3) are shaped and dimensioned such that when the filter (1) is deployed, the struts (3) expand radially and outwardly so that the footplates (13) at the distal ends of each of the struts (3) contact the vessel wall (23). Being that struts (3) may be of different length, the angle of each particular strut (3) relative to the central axis of the vessel will be greater for the shorter struts. An alternative embodiment would have struts of variable length, creating a helical arrangement at the points of contact with the vessel wall (23).

Figure 5:
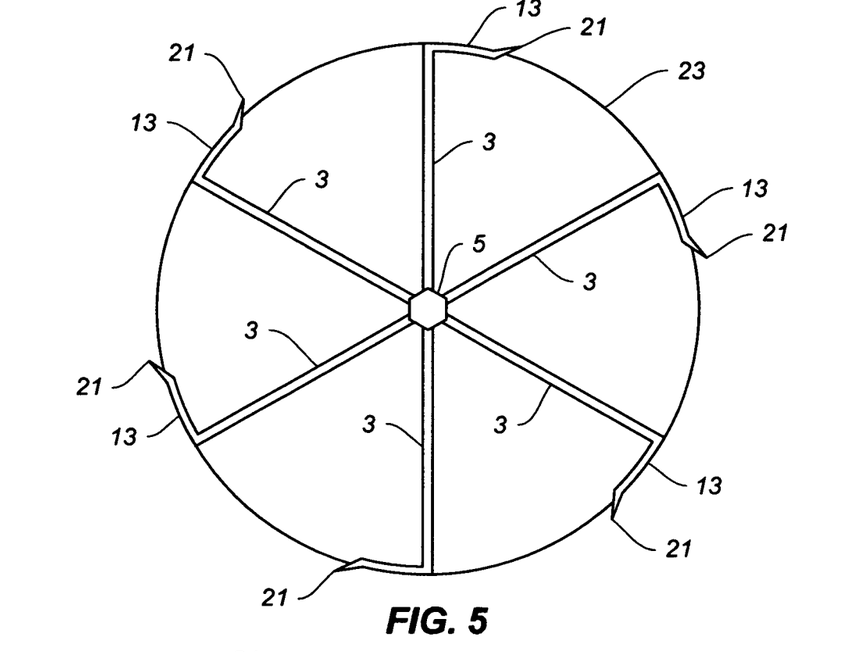
FIG. 5 is a cross sectional view of a blood vessel containing the embodiment of FIG. 1 within the blood vessel.
Figure 6:
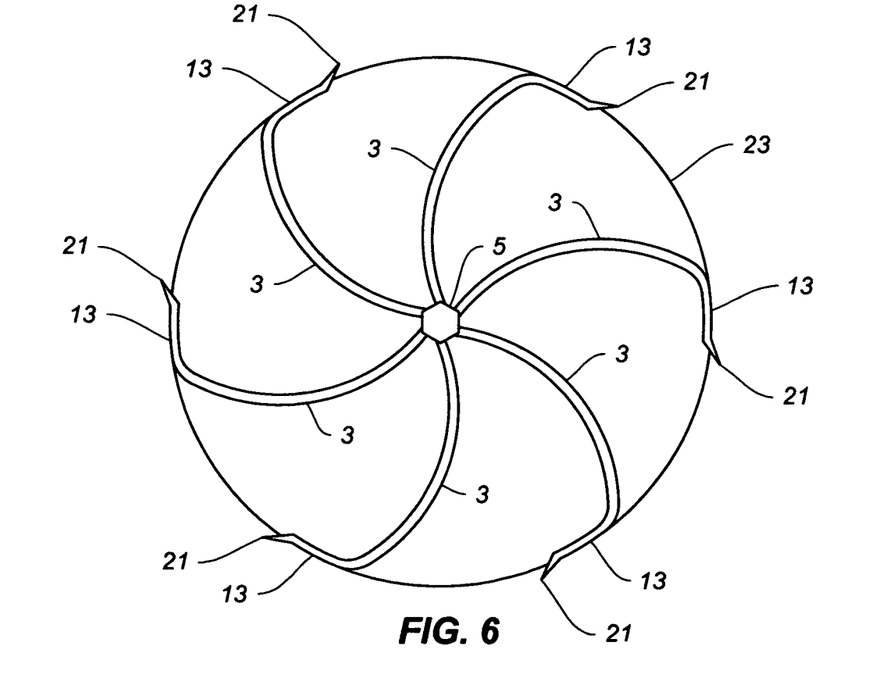
FIG. 6 is a cross sectional view of a blood vessel containing the embodiment of FIG. 4 within a blood vessel.

As depicted in FIG. 5, the struts (3) can emanate from the central hub (5) in a straight radial direction from the central axis. Alternatively, as depicted in FIG. 4 and FIG. 6, the struts (3) can emanate from the central hub (5) in an arc or curved shape to the vessel wall (23). The former may allow for a more compact arrangement in the collapsed state, thereby decreasing the size of the delivery system. In other embodiments, the struts (3) can emanate from the central hub (5) in a zigzag or any other linear or non-linear direction to the vessel wall (23).

Figure 7:
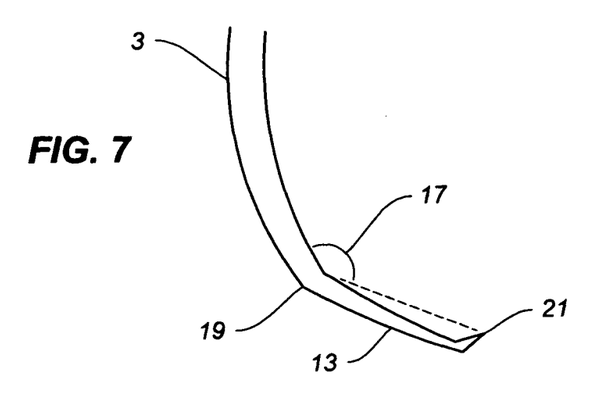
FIG. 7 is a magnified side view of an embodiment of the anchoring and centering footplate at the distal (upstream) end of each arced filter leg.

As shown in FIG. 7, the configuration whereby the struts (3) emanate from the central hub (5) in an arc or curved shape to the vessel wall (23) may decrease the angle (17) between the strut (3) and footplate (13). Such a configuration may better facilitate filter removal.

Figures 8, 9:
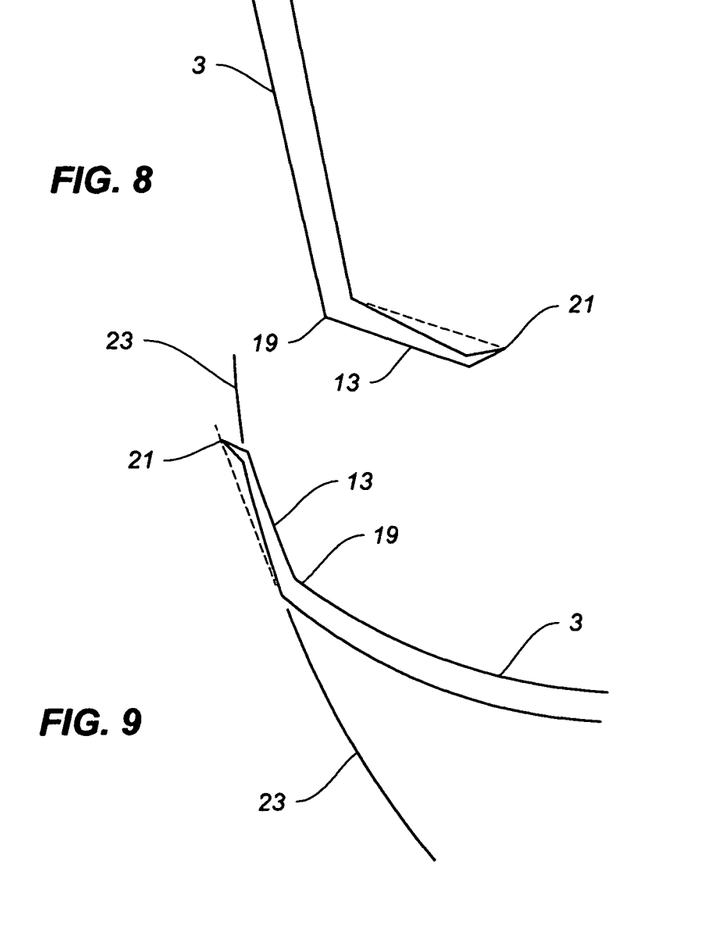
FIG. 8 is a magnified side view of an embodiment of the anchoring and centering footplate at the distal (upstream) end of each straight filter leg.
FIG. 9 is a magnified axial view of an embodiment to the anchoring footplate within a vessel.
Figure 10:
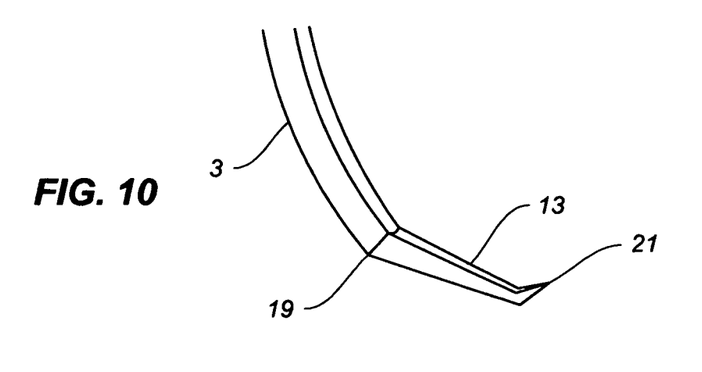
FIG. 10 is a 3-dimensional rendering depicting an embodiment of the tapering footplate.

FIG. 8 and FIG. 9 show alternative preferred embodiments of the distal footplate (13) in more detail. The footplate (13) is the distal end of the strut (3) and is the primary point or plane of contact between the filter and the vessel wall (23). In a preferred embodiment, the footplate (13) can be about 5-10 mm in length and is angled relative to the strut, so as to decrease the overall expanded length of the filter, and to minimize filter tilt. As depicted in FIG. 8, FIG. 9, and FIG. 10, the footplate (13) tapers in both height and thickness, such that the thickest and highest point of the footplate (13) is near the transition with the strut (19). As shown in FIG. 10, this gives the footplate (13) a conical or pyramidal shape, though other shapes for the footplate (13) may be employed in other embodiments. Ina preferred embodiment, the footplate (13) tapers to an anchoring hook (21) on the distal end which is adapted to press slightly into the wall of the vessel.

Figure 11:
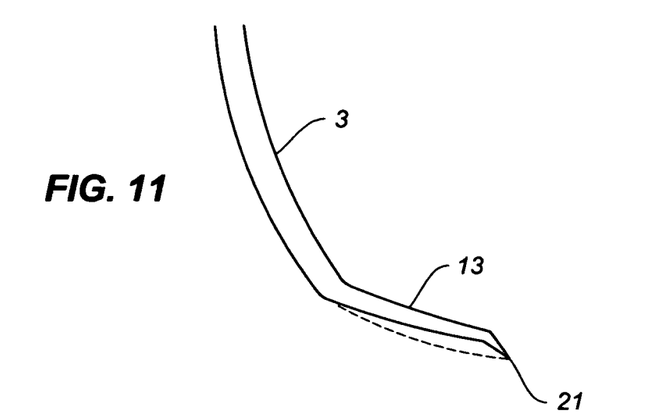
FIG. 11 is a side view of an embodiment of the anchoring and centering footplate, with the anchoring tip oriented in an upstream direction.

As illustrated in FIG. 8 and FIG. 9, the extent of the taper on the footplate (13) is such that the anchoring hook (21) does not extend beyond the plane defined by the width of the height of the footplate. In a preferred embodiment, the anchoring hook (21) also curves slightly outward, away from the central axis of the vessel, relative to the plane of the footplate (13), so as to engage the vessel wall (23). The spring biased configuration of the struts (3) facilitates engagement of anchoring hook (21) with the wall. As depicted in FIG. 8 and FIG. 11, the anchoring hook (21) can point either upstream or downstream, to prevent upstream and downstream migration, respectively. Any combination of upstream or downstream hooks can be utilized in order to minimize filter migration.

Figure 12:
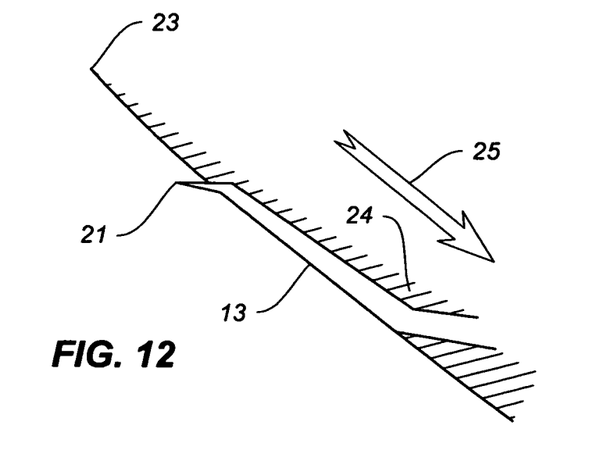
FIG. 12 depicts the footplate of FIG. 10 which has been enveloped with a fibrous sleeve.

FIG. 12 illustrates how a torque force can allow for retrieval of the filter. Tissue growth (24) will presumably occur along the footplate (13) and anchoring hook (21). The tapered configuration of the footplate facilitates withdrawal of the footplate from the fibrinous sleeve upon application of a torque and longitudinal force (25). Any retrieval mechanism which can capture the filter (with or without a snare), provides a torque and longitudinal force to free the filter from the vessel wall (23) and tissue sleeve, and secures the filter within a sheath, can be used to retrieve the filter.

Figure 13:
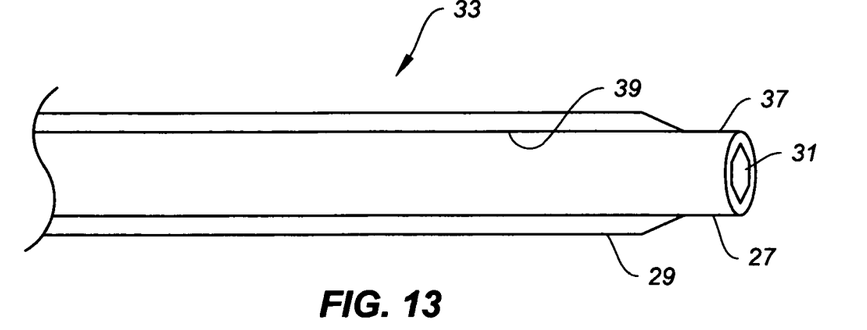
FIG. 13 is a side view of an embodiment of the retrieval sheaths for the filter of FIG. 1 and FIG. 4.
Figure 14:
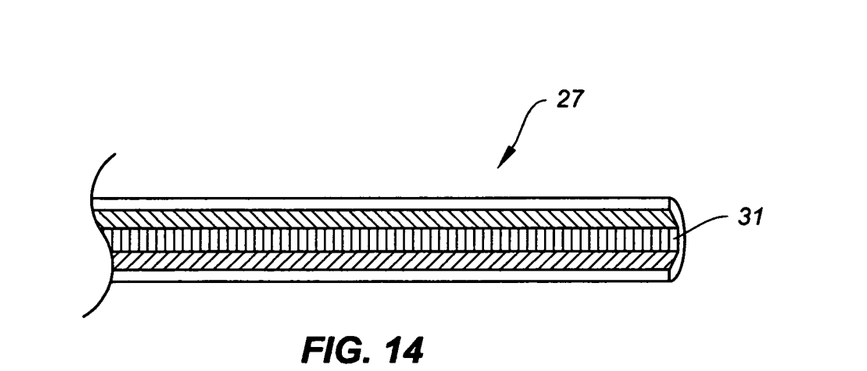
FIG. 14 is an internal view of one embodiment of the inner extracting catheter for filter removal.

FIG. 13 through FIG. 17 illustrate an embodiment of a system for removing the filter (1). The retrieval device consists of two coaxially introduced sheaths (27 and 29), where the outer diameter of the inner sheath (27) is in substantially in contact with the inner diameter of the outer sheath (29). The outer diameter of the outer sheath is the minimum which can be achieved while ensuring stability to the system. The inner diameter (31) of the inner sheath (27) is sufficient to accommodate a snare device. The retrieval device is percutaneously inserted, usually through the right internal jugular vein, but potentially through the common femoral vein, or any other suitable upstream or downstream access site. As depicted in FIG. 18, the retrieval system (33) is positioned in the IVC, superior to the filter (1). The snare is exited through the end of the sheath and is manipulated to ensnare the hook (11) on the filter (1). The coaxial sheaths of the retrieval device (33) are advanced over the snare wire and catheter (35), and over the filter hook (11), and engage the filter hub (5) with the distal end of the sheath. The inner lumen (31) of the inner sheath (27) is contoured to conform to the geometry of the filter hub (5). In FIG. 13 and FIG. 18, both the inner lumen (31) of the inner sheath (27), and the filter hub (5) are hexagonal in shape, though any shape that allows for transmission of a torque force is acceptable.

In the embodiment depicted in FIG. 13, the outer surface of the inner sheath (37) and the inner lumen of the outer sheath (39) are smooth. The filter is removed by the application of a rotational force on the inner sheath (27), in a direction conforming to the natural curve of the filter, and a longitudinal force directed craniad.

Figure 15:
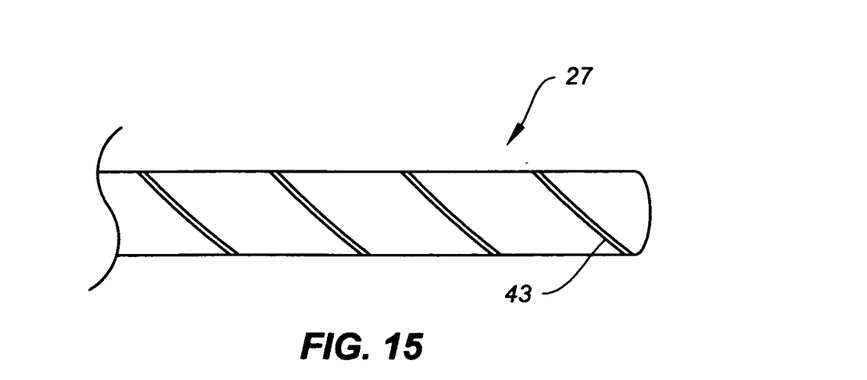
FIG. 15 is an external view of the embodiment of the extracting catheter of FIG. 14.
Figure 16:
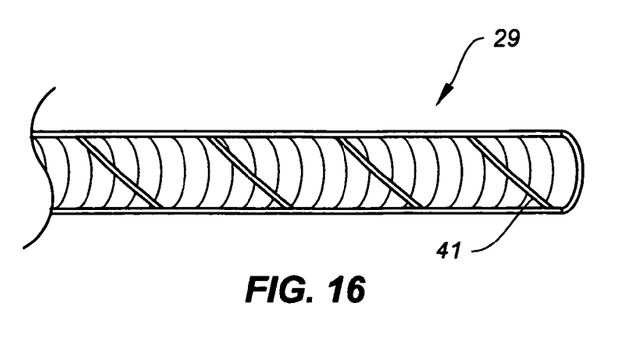
FIG. 16 is an internal view of one embodiment for the outer extracting catheter for filter removal.
Figure 17:
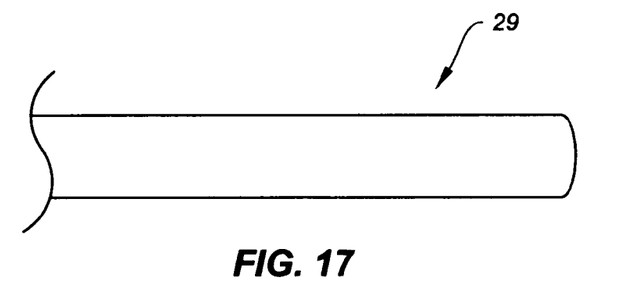
FIG. 17 is an external view of the extracting catheter of FIG. 16.
Figure 18:
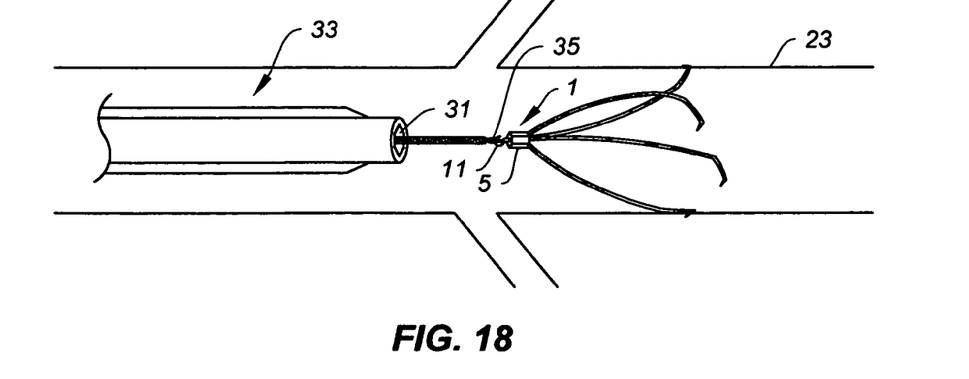
FIG. 18 is an illustration of the capture and extraction of the filter in a vessel.

In another embodiment, as illustrated in FIG. 15 through FIG. 17, there are matching grooves and threads along the inner diameter of the outer sheath (41) and along the outer diameter of the inner sheath (43). These threads can span the entire length of the sheath, or only a portion of the sheath. The pitch of the threads is such that the correct combination of torque and longitudinal force are imparted on the filter to facilitate withdrawal of the footplates from the tissue sleeve of the vessel. The filter may be ensnared in a similar fashion as described in connection with FIGS. 13-18 above.

FIG. 18 illustrates an embodiment of a snared filter. As described above, once the filter (1) is secured with the snare (35), the sheaths are advanced over the snare wire and catheter, and over the filter hook (11), so that the distal end of the inner sheath engages the filter hub (5). With the hub secured within the inner sheath, the inner sheath is twisted while holding the outer sheath stable, imparting a torque and longitudinal force to the filter until the filter is secured within the outer sheath. Although the design of FIG. 18 contemplates capture of the filter (1) with a snare device (35), any method of capturing the filter that would allow for subsequent engagement of the filter hub by the retrieval sheaths may be utilized.

Figure 19:
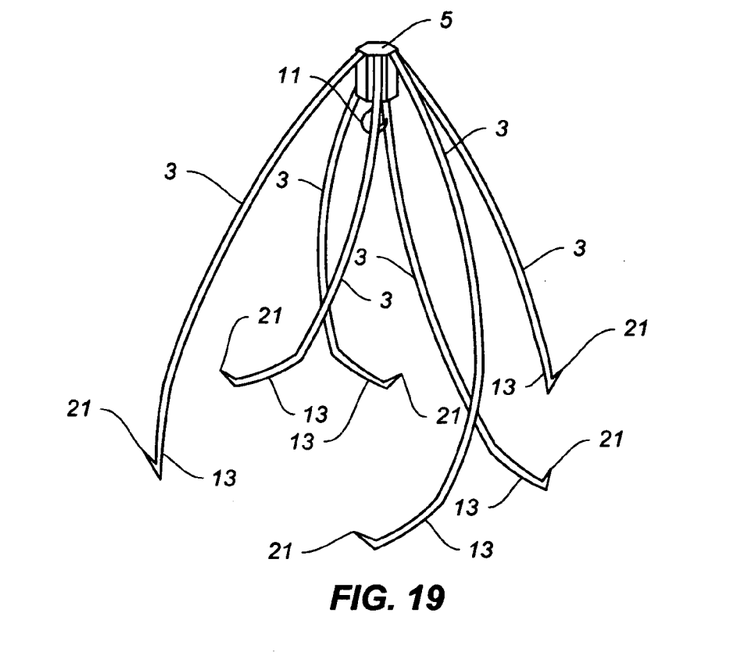
FIG. 19 is a side view of an alternative embodiment of the vascular filter described herein.
Figure 20A:
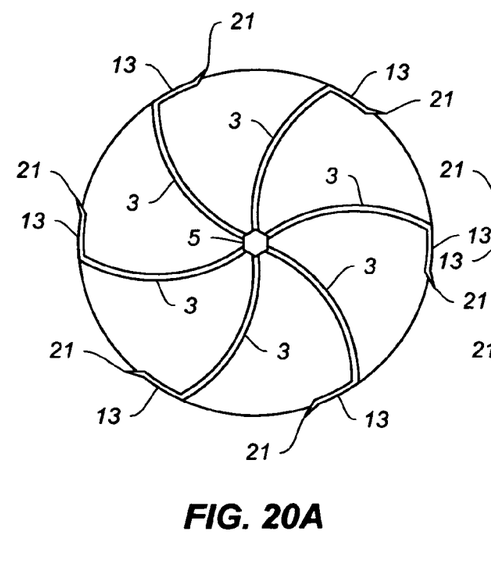
FIG. 20A is a cross sectional view of a blood vessel containing the embodiment of FIG. 19 within the blood vessel.
Figure 20B:
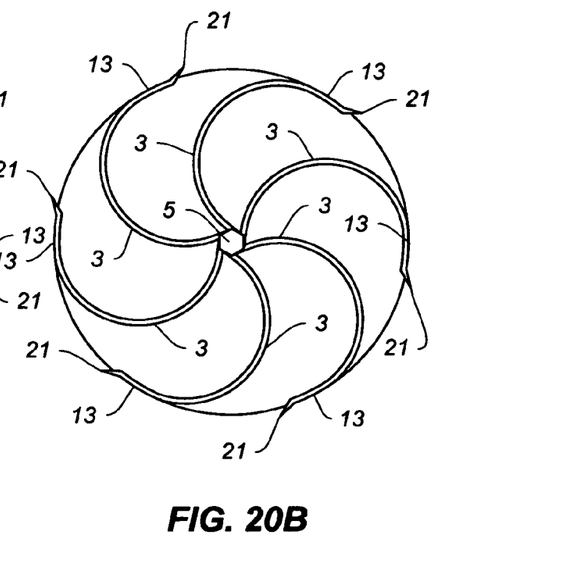
FIG. 20B is a cross section view of a blood vessel containing the embodiment of FIG. 20 within the blood vessel wherein torque has been applied to the filter hub thereby collapsing the struts somewhat along the longitudinal axis of the filter.

FIG. 19 depicts an alternative embodiment of a filter, wherein the capturing hook (11) is oriented in the upstream direction, to allow for extraction of the filter from a femoral vein approach. FIG. 20A depicts cross-sectional view of a vessel wall (23) with the embodiment of FIG. 19 embedded therein. As with the previous embodiment, the hook (11) is ensnared and the coaxial sheaths of the retrieval device are advanced over the snare wire and catheter, over the hook, until the filter hub (also oriented upstream in this embodiment), is engaged. For the embodiments depicted in FIGS. 19 and 20A, during retrieval, imparting a torque force on the hook (11) would wind the filter legs (3) into a state that creates a slightly shortened radius of the legs (3) relative to the longitudinal axis of the vessel, as depicted in FIG. 20B. This allows inversion of the filter when the snare is pulled in an upstream direction. Once the filter is inverted, application of a rotational and longitudinal force will cause withdrawal of the footplate from the vessel wall (23) and allow removal of the filter. In another embodiment, multiple hooks (11) may be utilized on either side of hub (5) to provide a choice with respect to the approach of retrieval.

While the foregoing written description of the invention enables one of ordinary skill to make use what is considered presently to be the best mode thereof, those of ordinary skill will understand and appreciate the existence of variations, combinations, and equivalents of the specific embodiment, method, and examples herein. The invention should therefore not be limited by the above described embodiments, methods and/or examples, but by all embodiments and methods within the scope and spirit of the invention as claimed.

I claim:

1. An intravascular filter for placement within a blood vessel, said filter comprising:
   a central hub;
   two or more struts extending from said hub;
   said struts having a distal end, the distal end of said struts being unconnected to the distal end of adjacent struts of said struts;
   the distal end of said struts being angled to form an anchor when placed in contact with a vessel wall, wherein said angle imparts a substantially hockey-stick shape to said struts.

2. The filter of claim 1, wherein a retrieval structure is attached to said hub.

3. The filter of claim 1, wherein said retrieval structure is a hook.

4. The filter of claim 1, wherein said retrieval structure is a loop.

5. The filter of claim 2, wherein said retrieval structure is attached to top end of said hub.

6. The filter of claim 2, wherein said retrieval structure is attached to bottom end of said hub.

7. The filter of claim 1 wherein two or more retrieval structures are attached to said hub.

8. The filter of claim 1 wherein said struts are of varying lengths.

9. The filter of claim 8, wherein said struts have distal ends that are angled.

10. The filter of claim 8, wherein a curved structure is attached to said hub for facilitating retrieval of said filter.

11. The filter of claim 8, wherein an angled structure is attached to said hub for facilitating retrieval of said filter.

12. The filter in claim 1, wherein there are four or more struts extending from said hub.

13. The filter in claim 12, wherein said struts are of alternating length relative to said hub.

14. The filter in claim 1, wherein said distal end of said struts are oriented in varying directions with respect to the longitudinal axis of said filter.

15. The filter of claim 1, wherein said distal end of said struts have a conical shape.

16. The filter of claim 1, wherein said distal end of said struts are oriented in the same direction with respect to the longitudinal axis of said filter.

\* \* \* \* \*